United States Patent [19]

Rheinberger et al.

[11] Patent Number: 5,354,785
[45] Date of Patent: Oct. 11, 1994

[54] POLYMERIZABLE DENTAL MATERIALS

[75] Inventors: Volker Rheinberger, Vaduz, Liechtenstein; Ulrich Salz, Weissenberg, Fed. Rep. of Germany; Kurt Grabher, Feldkirch, Austria

[73] Assignee: Ivoclar A.G., Schaan, Liechtenstein

[21] Appl. No.: 970,236

[22] Filed: Nov. 2, 1992

Related U.S. Application Data

[63] Continuation of Ser. No. 674,133, Mar. 25, 1991, abandoned.

[30] Foreign Application Priority Data

Mar. 26, 1990 [DE] Fed. Rep. of Germany ....... 4009602

[51] Int. Cl.$^5$ ............... A61K 6/083; C08K 3/22
[52] U.S. Cl. ............... 523/116; 523/115; 524/405; 524/433; 524/443; 524/494; 524/779
[58] Field of Search ........... 523/115, 116; 524/779, 524/405, 443, 494, 433

[56] References Cited

U.S. PATENT DOCUMENTS

| | | | |
|---|---|---|---|
| 4,215,033 | 7/1980 | Bowen | 523/115 |
| 4,755,620 | 7/1988 | Iwamoto et al. | 523/116 |
| 4,918,136 | 4/1990 | Kawaguchi et al. | 523/116 |
| 5,013,782 | 5/1991 | Tateno | 524/417 |
| 5,192,815 | 3/1993 | Okada et al. | 523/115 |

FOREIGN PATENT DOCUMENTS

| | | |
|---|---|---|
| 0091990 | 10/1983 | European Pat. Off. |
| 0189903 | 8/1986 | European Pat. Off. |
| 2454101 | 5/1975 | Fed. Rep. of Germany. |
| 236891 | 2/1978 | Fed. Rep. of Germany. |
| 0055964 | 4/1982 | Japan ................... 524/443 |
| 109417 | 11/1987 | Japan. |
| WO9000893 | 2/1990 | PCT Int'l Appl. |

OTHER PUBLICATIONS

E. C. Combme Zahnarztliche Werkstoffe, Hanser Verlag, Munich (1984) 134–136 Search Report.

*Primary Examiner*—Paul R. Michl
*Assistant Examiner*—Andrew E. C. Merriam
*Attorney, Agent, or Firm*—Cushman, Darby & Cushman

[57] ABSTRACT

Polymerizable dental materials, suitable as underfilling material, comprising at least one polymerizable monomer or prepolymer, a setting catalyst and inorganic fillers comprise as filler, a glass powder comprising of 40-75 wt-% CaO, 5-30 wt-% $B_2O_3$ and 5-35 wt-% $SiO_2$.

10 Claims, No Drawings

POLYMERIZABLE DENTAL MATERIALS

This is a continuation of application Ser. No. 07/674,133, filed on Mar. 25, 1991, now abandoned.

The invention relates to dental materials with an alkalizing effect such as e.g. cements, cavity liners and root filling materials, in particular a polymerizable dental materials suitable as underfilling material, based on at least one polymerizable monomer or pre-polymer, a hardening catalyst and inorganic fillers.

When treating tooth cavities, underfilling materials serve to cap the pulpa before the actual filling is laid. It is known that calcium hydroxide is responsible for the formation of secondary dentin over the pulpa and that the thicker and more solid this layer is, the better the protection. However, the calcium-hydroxide-containing cements usually used, which harden on a chelate basis, do not provide satisfactory hardness.

In published European Application 189 903 a photopolymerizable underfilling material comprising calcium hydroxide or a calcium-hydroxide-forming agent such as calcium oxide is described. This underfilling material contains ethylenically unsaturated compounds, in particular vinyl compounds, as well as a photocatalyst, e.g. camphorquinone in combination with an amine. A basic problem is, however, that calcium hydroxide or calcium oxide are very opaque, so that only low curing depths can be obtained, as trials with a trade product according to EP-A-189 900 903 (Prisma VLC Dycal ® from Dentsply International, Inc.) show.

It is an object of the invention to provide an underfilling material which is hydrolysis- and acid-resistant, has low water-solubility, displays good compressive strength and is non-toxic. Moreover, a controlled release of calcium hydroxide is to be achieved, in order to obtain an alkalizing effect vis-a-vis the pulpa and to protect the latter against acids and bacterial attacks. In particular, the material is to have a higher curing depth and lower shrink after polymerisation.

It was surprisingly found that this aim can be achieved by incorporating into the dental materials, as filler, a glass powder with a high content of calcium oxide. The glass powders used according to the invention are not opaque and therefore do not impair the light curing of the dental materials.

The glass powder used according to the invention comprises, in addition to 40 to 75 wt-% calcium oxide, 5 to 30 wt-% boron oxide and 5 to 35 wt-% silica. A preferred composition consists of 45 to 60 wt-% calcium oxide, 15 to 28% boron oxide and 10 to 30 wt-% silica.

The average particle size (mean weight) of the glass powders lies preferably between approximately 10 and 30 um, but powders with a particle size of 1 to 100 um are suitable.

As already mentioned above, the dental materials according to the invention are, because of the controlled release of calcium oxide or hydroxide from the glass powder, particularly suited as underfilling material. They are preferably light curable single-component materials. These optionally comprise in addition to the glass powder further inorganic fillers and at least one polymerizable monomer or prepolymer and suitable catalysts.

Further, the glass can optionally comprise oxides, e.g. kaolin or oxides of Sr, Ba, La, Zr or rare earths. Ca-tungstate, Ba-tungstate and fluorine- and/or phosphorus-containing compounds such as e.g. NaF, KF, $BaF_2$, $SrF_2$, the fluorides of rare earths, Ca- or Al-phosphate and cryolite are further suitable additives.

The fluorides of the rare earth metals (RE) with the atomic numbers 59 to 71 have proved especially suitable as inorganic fillers, preferred compounds being those of the elements 66 to 71.

Preferably, ytterbium fluoride is used. The fluorides of the rare earth metals are generally incorporated as powder into the dental material. The average particle size of the primary particles can vary. For a micro-filled tooth-filling material it lies in the range from 5 to 700, particularly 20 to 500, preferably 50 to 300 nm. Optionally, the average primary particle size can also lie in the range from 700 nm to 15 um.

The RE fluorides content, relative to the total weight, is between 1 and 50%, particularly 5 to 40%; preferably, it lies between 10 and 30%. It particularly depends on the desired X-ray-opacity or transparency. Mixtures of the RE fluorides can also be used.

Other fillers such as Ba-, Sr-, Ca-, Li-Al-silicate glasses and $BaSO_4$, $CaWO_4$, Bi subnitrate and-Bi carbonate can also be used.

Other non-X-ray-opaque inorganic constituents are usually present in the dental materials. Suitable as fillers are e.g. amorphous silicas, particularly pyrogenic or precipitated silica with a BET surface of approximately 20 to 400 $m^2/g$. In particular, pyrogenic silicas with a BET surface of 30 to 300 $m^2/g$ and an average particle size of the primary particles of approximately 5 to 50 nm are used, specially preferred materials lying in the range between 1 and 50 nm. Silicas with an average primary particle size of 50 to 1000, preferably 100 to 300 nm can, however, likewise be used. Li-Al-silicate glasses are likewise suitable, as previously mentioned.

The quantity of non-X-ray-opaque fillers in the dental material depends on the quantity of the RE fluorides used and generally varies in the range from 5 to 84 wt-%, particularly 10 to 70 wt-%, preferably 20 to 50 wt-%. In total the content of fillers (glass powders, RE fluorides and other inorganic compounds) is 6 to 85 wt-%, preferably 15 to 85 and particularly 30 to 85 wt-%.

The inorganic constituents of the dental material can be silanized in the usual way, to improve the bond between organic matrix and inorganic filler. Suitable as adhesion promoter is e.g. 3-methacryloxypropyltrimethoxysilane. The quantity of adhesion promoter used depends on the type and the specific surface of the filler and the desired viscosity of the dental material.

The dental materials must further contain a polymerizable vinyl compound. For this monofunctional or polyfunctional (meth)acrylates, which can be used alone or in mixtures, are suitable. Examples of these compounds which come into consideration are: methyl methacrylate, isobutyl methacrylate, cyclohexyl methacrylate, triethylene glycol dimethacrylate, diethylene glycol dimethacrylate, tetraethylene glycol dimethacrylate, ethylene glycol dimethacrylate, polyethylene glycol dimethacrylate, butanediol dimethacrylate, hexanediol dimethacrylate, decanediol dimethacrylate, dodecanediol dimethacrylate, bisphenol-A-dimethacrylate, trimethylol propane trimethacrylate, ethoxylated bisphenol-A-dimethacrylate and also bis-GMA (2,2-bis-4-(3-methacryloxy-2-hydroxypropyl)-phenylpropane) as well as the reaction products of isocyanates, in particular di- and/or triisocyanates and OH-group-containing methacrylates. Examples of these are the reaction products of 1 mol hexamethylene diisocyanate with 2 mol 2-hydroxyethyl methacrylate, of 1 mol tri(6-isocyanatohexyl)biuret with 3 mol hydroxyethyl methacrylate and of 1 mol trimethylhexamethylene diisocyanate with 2 mol hydroxyethyl methacrylate, which are henceforth described as urethane dimethacrylate. The proportion of these mostly long-chained compounds in the dental material varies between 10 and 50 wt-%. In principle, all binders usable for a dental material are suitable.

The dental material can be hot- or cold-curable or curable by photopolymerisation. However, combinations of these are also possible (dual curing).

As catalysts for hot polymerisation, the known peroxides such as dibenzoyl peroxide, dilauroyl peroxide, tert.-butylperoctoate or tert.-butylperbenzoate can be used, and $\alpha,\alpha'$azo-bis-(isobutyroethylester), benzopinacol and 2,2'-dimethylbenzopinacol are also suitable.

As catalysts for photopolymerisation, e.g. benzophenone and derivatives thereof, acyl phosphinoxides and also benzoin and derivatives thereof can be used. Examples of preferred photoinitiators are the $\alpha$-diketones such as 9,10-phenanthrenequinone, diacetyl, furil, anisil, 4,4'-dichlorobenzil and 4,4'-dialkoxybenzil. It is especially preferred to use camphorquinone. The use of the photoinitiators together with a reducing agent is preferred. Examples of reducing agents are amines such as cyanethylmethylaniline, dimethylaminoethyl methacrylate, triethylamine, triethanolamine, N,N-dimethylaniline, N-methyldiphenylamine and N,N-dimethyl-sym.-xytidine, N,N-dimethyl-p-toluidine and p-dimethylaminobenzoic acid ethyl ester. As catalyst mixtures the photoinitiators and reducing agents can be used together with catalysts for hot polymerisation (preferably with peroxides).

As catalysts for cold polymerisation, radical-supplying systems, e.g. benzoyl or lauroyl peroxide together with amines such as N,N-dimethyl-sym.-xylidine, N,N-di-2-hydroxyethyl-p-toluidine or N,N-dimethyl-p-toluidine are used.

The quantity of these catalysts in the dental material usually lies between 0.1 and 5 wt-%.

Finely divided chip or bead polymers, which can be homo- or copolymers of the previously described vinyl compounds, can also be incorporated into the dental material. These homo- or copolymers can for their part be filled with the described inorganic, and also the X-ray-opaque, fillers. Reference is made to European patent 11 190 and German patent 24 03 211. Further, the dental material may comprise the usual pigments and stabilizers.

In order to increase the degree of filling of such dental materials, it is usual to prepare a copolymer from e.g. bis-GMA, triethylene glycol dimethacrylate, the glass powder and optionally other inorganic fillers such as ytterbium fluoride and pyrogenic silica, to grind this copolymer as chip polymer and then to incorporate it into the dental filling material.

With light curable materials, polymerization takes place with a standard commercially available halogen lamp after the underfilling has been laid.

Filling materials are also prepared as two-component materials which cold-set after mixing together. The composition is similar to that of the light-setting materials, except that, instead of the photocatalysts, e.g. benzoyl peroxide is mixed into one paste and e.g. N,N-dimethyl-p-toluidine into the other paste. By mixing almost equal parts of the two pastes, a dental filling material is obtained which cures in a few minutes.

The following examples serve to illustrate the invention.

EXAMPLES

To produce the glasses used according to the invention as filler the raw materials were mixed together in a ball mill, and the mixtures subsequently sintered for one hour at 1000° C. in a crucible made of aluminium oxide. The pre-sintered mixtures were once again homogenized. Subsequently the mixtures were melted in a platinum crucible (30 mins at 1500° C.). The melts were quenched in water, the materials were dried and finally dry-ground in a ball mill. Calcium carbonate, quartz and boron oxide are suitable as raw materials. If need be, small quantities of up to 5 wt-% of a fluxing agent such as e.g. cryolite, NaF, KF etc. are added. The proportion of calcium carbonate is so high that the $CaO:SiO_2$ ratio is normally over 1.5.

The glasses were uniformly mixed with a polymerizable vinyl compound (monomer). Other inorganic substances were added to some mixtures. The monomer for tests A to F and H to K was a mixture of 2,2-bis[p-($\beta$-hydroxyethoxy)phenyl]propane-di-methacrylate (SR 348) and a urethane dimethacrylate (RM3) (reaction product of trimethylhexamethylene diisocyanate and hydroxy ethyl methacrylate). The monomer in test G was a mixture of 56.6 g of 2,7,7,9,15-pentamethyl-4,13-dioxo-3,14-dioxa-5,12-diaza-hexadecane-1,16-diyl-dimethacrylate and 5 g of 3,6-dioxaoctamethylene dimethacrylate. Comparison test G was carried out with the commercial product Prisma VLC Dycal ® (De Trey Dentsply). Test A is likewise a comparison test representing the prior art.

Camphorquinone (CQ) and cyanoethyl methylaniline (CEMA) served as photo initiators. The binding agent for tests A to F and H to K had the following composition:

| SR 348 | 80.0 wt-% |
|---|---|
| RM3 | 19.17 wt-% |
| CQ | 0.3 wt-% |
| CEMA | 0.5 wt-% |
| BHT | 0.03 wt-% |

BHT = 2,6-di-tert.-butyl-p-cresol (stabilizer)

For measuring the curing depth, transparency, compressive strength, water-solubility, water absorption and $Ca(OH)_2$ release test specimen were manufactured. The manufacture of the test specimen and their dimensions:

Curing depth—steel mould diameter 4 mm, height 6 mm. The mould is filled and exposed for 40 seconds with a standard commercially-available light-setting lamp (Heliomat ® from Vivadent).

Transparency—the test specimen is manufactured in a steel mould measuring 15×9×1 mm and set under 6 bar pressure for 3 minutes in a light-setting apparatus. Transparency was measured with an apparatus as described in published European Patent Application 189 540, Example 1.

Compressive strength—test specimen are manufactured in a Delrin ® mould with a diameter of 4mm and a height of 6 mm. The material was cured for 3 minutes with the light-setting apparatus.

Water-solubility and water absorption—The test specimen is manufactured in a steel mould with a diameter of 15 mm and a height of 0.5 mm. Curing takes place as described above.

The test results can be seen in Tables I and II.

Discussion on the test results

The tests show, for the underfilling materials according to the invention, with regard to through curing depth, transparency and compressive strength, almost the same values as are obtained with $Ca(OH)_2$ as filler (test A). The underfilling materials according to the invention are superior with regard to most properties to the commercial product Prisma VLC Dycal ® (test G).

The products according to the invention are clearly better in terms of water-solubility and water absorption and in particular the release of calcium hydroxide.

alkalizing effect on the pulpa protecting the pulpa against acids and bacterial attacks.

2. A method according to claim 1, wherein the inorganic filler materials are glass powders comprising:
45–60 wt-%, CaO,
16–28 wt-%, $B_2O_3$,
10–30 wt-%, $SiO_2$.

3. A method according to claim 2, wherein the inorganic filler materials essentially consists of CaO, $B_2O_3$, and $SiO_2$.

4. A method according to claim 1, wherein the inorganic filler materials comprises other inorganic fillers.

5. A method according to claim 4, wherein the inorganic filler materials comprises other inorganic fillers selected from the group comprising ytterbium fluoride,

TABLE I

|  | A | B | C | D | E | F | G |
|---|---|---|---|---|---|---|---|
| Monomer | 30% | 35% | 30% | 30% | 20% | 25% | 61.6% |
| CaO |  | 45.0 | 59.4 | 55.2 | 45.0 | 45.0 |  |
| $B_2O_3$ glass |  | 26.5 40% | 25.6 70% | 21.7 70% | 26.5 50% | 26.5 50% |  |
| $SiO_2$ |  | 28.5 | 15.0 | 23.1 | 28.5 | 28.5 |  |
| $YbF_3$ |  | 25% |  |  |  |  |  |
| $BaSO_4$ | 20% |  |  |  |  |  | 18.9 |
| Ba-glass |  |  |  |  | 30% |  |  |
| Aerosil OX50 ® |  |  |  |  |  | 25% |  |
| $Ca(OH)_2$ | 50% |  |  |  |  |  | 18.9 |
| Through-setting depth | 3.4 ± 0.1 | 3.1 ± 0.1 | 2.7 ± 0.1 | 3.1 ± 0.1 | 3.5 ± 0.2 | 2.7 ± 0.1 | 1.8 ± 0.1 |
| Transparency % | 28 ± 1 | 29 ± 1 | 19 ± 1 | 21 ± 1 | 25 ± 1 | 19 ± 1 | 21 ± 1 |
| Compressive strengh N/mm² |  |  |  |  |  |  |  |
| after 24 h | 137 ± 2 | 173 ± 7 | 119 ± 3 | 117 ± 8 | 224 ± 13 | 254 ± 6 | 180 ± 8 |
| after 1 week | 161 ± 8 | 174 ± 8 | 125 ± 5 | 105 ± 10 | 242 ± 12 | 253 ± 18 | 190 ± 9 |
| Deformation at 200N |  |  |  |  | 7 ± 0.2% | 9 ± 1% |  |
| Bending strength N/mm² |  |  |  |  | 75 ± 7 |  | 29 ± 4 |
| Bending modulus N/mm² |  |  |  |  | 8500 ± 500 |  | 910 ± 170 |
| $H_2O$ solubility after 24 hours | 1.2 ± 0.3 | 0.15 ± 0.05 | 0.75 ± 0.04 | 0.8 ± 0.3 | 0.1 ± 0.05 | 0.1 ± 0.04 | 0.25 ± 0 |
| $H_2O$ absorption after 24 hours | 1.3 ± 0.3 | 0.6 ± 0.1 | 0.2 ± 0.06 | 0.35 ± 0.1 | 0.3 ± 0.05 | 0.3 ± 0.05 | 2.3 ± 0.25 |

TABLE II

|  | H | J | K | G |
|---|---|---|---|---|
| Monomer | 30% | 30% | 30% | s.Tab.1 |
| CaO | 59.4 | 59.4 | 55.2 |  |
| $B_2O_3$ glass | 19.6 70% | 25.6 70% | 21.7 70% |  |
| $SiO_2$ | 21.0 | 15.0 | 23.1 |  |
| $Ca(OH)_2$ discharge (ppm) after |  |  |  |  |
| 1 day | 101.3 | 154.6 | 182.7 | 34.0 |
| 2 days | 238.4 | 289.3 | 277.5 | 61.0 |
| 3 days | 307.2 | 379.2 | 324.8 | 74.6 |
| 4 days | 343.7 | 424.8 | 370.2 | 86.4 |
| 11 days | 431.4 | 550.5 | 501.5 | 114.0 |
| 25 days | 502.9 | 631.1 | 575.6 | 115.0 |
| 8 weeks | 596.9 | 744.6 | 681.6 | 119.5 |

In each case two test specimens (∅ 20 mm, h = 1 mm) are suspended in 50 ml distilled $H_2O$. After varying intervals, the solution was back-titrated with 0.01 HCl and the consumption calculated as $Ca(OH)_2$. The samples were stored at 37° C. After each measurement the $H_2O$ was renewed.
The $Ca(OH)_2$ discharge is given cumulatively.

We claim:

1. A method for treating tooth cavities comprising applying underfilling material, wherein the underfilling material comprises:
   (a) a polymerizable dental material comprising a monofunctional (meth)acrylate, or a polyfunctional (meth)acrylate, or mixtures thereof;
   (b) a curing catalyst; and
   (c) an inorganic filler material comprising a glass powder comprising:
   40–75 wt-% CaO,
   5–30 wt-% $B_2O_3$,
   5–35 wt-% $SiO_2$,
   whereby the underfilling material provides a controlled release of calcium oxide or hydroxide for an barium sulphate, silica, and X-ray-opaque or non-X-ray-opaque dental glasses.

6. A method according to claim 5, wherein the catalyst is light curable.

7. A method according to claim 6, wherein the catalyst are photocatalyst and comprises camphorquinone, in combination with an amine.

8. A method according to claim 1, wherein said at least one photopolymerizable monofunctional or polyfunctional (meth)acrylate is present in a quantity of 10 to 50 wt-%.

9. Dental underfilling material for treating tooth cavities comprising:
   (a) a polymerizable dental material comprising a polymerizable monofunctional (meth)acrylate, or polyfunctional (meth)acrylate, or mixtures thereof,
   (b) a curing catalyst, and
   (c) an inorganic filler materials comprising a glass powder comprising:
   40–75 wt-% CaO,
   5–30 wt-% $B_2O_3$,
   5–35 wt-% $SiO_2$,
   whereby the underfilling material provides a controlled release of calcium oxide or hydroxide for an alkalizing effect on the pulpa protecting the pulpa against acids and bacterial attacks.

10. Dental underfilling materials according to claim 9, wherein the inorganic filler materials are a glass powder comprising:
   45–60 wt-% CaO,
   15–28 wt-% $B_2O_3$,
   10–30 wt-% $SiO_2$.

* * * * *